US011815210B2

(12) United States Patent
Knorth et al.

(10) Patent No.: US 11,815,210 B2
(45) Date of Patent: Nov. 14, 2023

(54) COUPLING FOR COUPLING OF ONE OR MORE HOSES TO A CLEANING MACHINE

(71) Applicant: Wassenburg Medical B.V., Dodewaard (NL)

(72) Inventors: Henny Hermanus Hendrik Knorth, Dodewaard (NL); Martijn Louis Jozef Martinus Roersch, Dodewaard (NL)

(73) Assignee: Wassenburg Medical B.V., Dodewaard (NL)

( * ) Notice: Subject to any disclaimer, the term of this patent is extended or adjusted under 35 U.S.C. 154(b) by 47 days.

(21) Appl. No.: 17/379,293

(22) Filed: Jul. 19, 2021

(65) Prior Publication Data

US 2022/0042634 A1     Feb. 10, 2022

(30) Foreign Application Priority Data

Jul. 20, 2020   (NL) ...................................... 2026093

(51) Int. Cl.
*F16L 37/084*      (2006.01)
*F16L 43/02*       (2006.01)
*A61B 1/12*        (2006.01)

(52) U.S. Cl.
CPC .......... *F16L 37/0847* (2013.01); *F16L 43/02* (2013.01); *A61B 1/123* (2013.01)

(58) Field of Classification Search
CPC ...... F16L 37/0847; F16L 43/02; A61B 1/123; A61B 1/00128; A61B 1/125; A61B 90/70; A61B 2090/701
See application file for complete search history.

(56) References Cited

U.S. PATENT DOCUMENTS

| | | | | |
|---|---|---|---|---|
| 2,374,225 A | * | 4/1945 | Melsom | F16L 33/2076 285/259 |
| 4,343,498 A | * | 8/1982 | Campanini | F16L 27/0816 285/272 |
| 4,635,973 A | * | 1/1987 | Sauer | F16L 33/22 285/322 |
| 5,137,309 A | * | 8/1992 | Beagle | F16L 33/2076 285/259 |
| 5,879,033 A | | 3/1999 | Hansel et al. | |

(Continued)

FOREIGN PATENT DOCUMENTS

EP    0271157 A1    6/1988
EP    2098185 A1    9/2009

*Primary Examiner* — James M Hewitt, II
(74) *Attorney, Agent, or Firm* — THE WEBB LAW FIRM

(57) ABSTRACT

A coupling for coupling one or more hoses to a cleaning machine including at least one connector for the connecting of a hose to be cleaned with a pillar and at least one pillar for the connection of the connector with a cleaning machine, wherein the pillar includes a longitudinal hollow body with at least two open ends including; a longitudinal guidance part, situated towards a first end; and a second end opposite to the first end in longitudinal direction; wherein the guidance part is provided with a thickening for the fixing of the connector to the guidance part, which thickening includes a first slope facing the first end, which slope has an angle with the guidance part between 5 and 45 degrees; and includes a second slope facing the second end, which slope has an angle with the guidance part between 30 and 60 degrees.

14 Claims, 3 Drawing Sheets

(56) References Cited

U.S. PATENT DOCUMENTS

| | | | | |
|---|---|---|---|---|
| 7,293,299 B2* | 11/2007 | Trickel | .................... | B60R 15/04 |
| | | | | 285/133.11 |
| 2013/0307265 A1 | 11/2013 | Sekino | | |
| 2015/0068022 A1 | 3/2015 | Menor | | |
| 2016/0143512 A1* | 5/2016 | Cheng | .................... | A61B 1/015 |
| | | | | 600/125 |

\* cited by examiner

COUPLING FOR COUPLING OF ONE OR MORE HOSES TO A CLEANING MACHINE

CROSS-REFERENCE TO RELATED APPLICATION

This application claims priority to The Netherlands Patent Application No. 2026093 filed Jul. 20, 2020, the disclosure of which is hereby incorporated by reference in its entirety.

BACKGROUND OF THE INVENTION

Field of the Invention

This invention relates to a coupling for coupling one or more hoses to a cleaning machine, a cleaning machine provided with such a coupling and a pillar for such coupling. The present invention in particular relates to coupling elements to be used in endoscope cleaning machines.

Description of Related Art

Medical devices, such as endoscopes, need to be treated, in particular rinsed, cleaned and sterilized, after use. To that end typically washing or cleaning machines are used, to automatically rinse or clean used equipment. An example of such machine is for instance known from EP0271157. In such a machine, a washing medium is prepared and fed to a washing post, washing outlet or pipe connection on a washing section of the machine. This post, outlet or pipe is then typically connected to the instrument to be treated, for instance to a connector in the endoscope.

SUMMARY OF THE INVENTION

The present invention aims to provide an improved coupling between a cleaning machine and devices to be treated.

The invention thereto provides a coupling for coupling one or more hoses to a cleaning machine comprising at least one connector for the connecting of a hose to be cleaned with a pillar and at least one pillar for the connection of the connector with a cleaning machine, wherein the pillar comprises a longitudinal hollow body with at least two open ends comprising; a substantially longitudinal guidance part, situated towards a first end, for the guidance of the connector over the pillar; and a second end opposite to the first end in longitudinal direction, for connecting the pillar to a cleaning machine; and wherein the guidance part is provided with a thickening for the fixing of the connector to the guidance part, which thickening comprises a first slope facing the first end, which slope has an angle with the guidance part between 5 and 45 degrees, preferably between 15 and 25 degrees and even more preferably substantially 20 degrees, for guiding the connector over the thickening from the first end of the guidance part; and comprises a second slope facing the second end, which slope has an angle with the guidance part between 30 and 60 degrees, preferably between 40 and 50 degrees, even more preferably substantially 45 degrees for creating a predetermined resistance to prevent undesired shifting of the connector with the pillar, especially undesired shifting in the direction towards the first end.

During cleaning it is preferable that the hose remains coupled to the machine, even though the coupling is exposed to increased pressures. For this purpose, hoses can be coupled to the pillars in a tight manner, which allows them to resist high pressures, but also makes it difficult to uncouple the hose from the cleaning machine. It is a drawback of such systems that it is not possible to use one hand only for the coupling since it takes a lot of force to uncouple the hose from the cleaning machine.

The angles of the slopes on both sides of the thickening can be chosen together with the material properties of the pillar and the connector, such that a balance is created between the ease of use in coupling and decoupling on one hand and on the other hand good sealing properties in the coupled state. To that end, each slope may serve a different function. The first slope for instance increases ease of use by smoothening mainly the coupling action of the user, with a gradual increase in thickness to gradually increase the force required to push the hose onto the pillar. The second slope for instance increases the resistance to prevent undesired uncoupling, wherein the slope is typically steeper than the first slope, putting up a resistance to prevent uncoupling. The angles of the first and second slope should be understood as an angle measured from the plane of the slope with an imaginary axis through the hollow body in the longitudinal direction, or alternatively the angle may be determined between the slope and a tangential line along the outside of the body.

When there is a movement in the direction from the second end to the first end (so a movement away from the pillar), the thickening will cause a resistance in this movement, thus preventing undesired shifting towards the first end in a coupled state. The angle of the second slope of preferably substantially 45 degrees creates a resistance such that it is possible to facilitate that the connector may be uncoupled from the pillar when desired because the created resistance can be overcome by the force of at least one hand. Advantage of the coupling according to the present invention is that it is possible to couple and uncouple the hose with one hand. Preferably the connector is substantially symmetrical in design, such that there is no difference for a right-handed or left-handed user. As a result, the coupling is user friendly for both left- or right-handed users.

In a coupled state a cleaning liquid is guided through the pillar, the connector to the hose for cleaning the hose coupled to the pillar. The coupling according to the present invention provides a balance between better sealing properties in coupled state and the possibility to uncouple the connector from the pillar without using a large force. The construction of the guidance part of the pillar increases the ease of use by the prevention of buckling. The connector may have at least two free ends, one of which is to be connected to the pillar. Another free end of the connector may be used to couple the connector with a device to be cleaned with the cleaning machine. That free end may for instance be used to attach to a cleaning port or cleaning attachment of an endoscope to be cleaned. That free end may also be used to couple the connector to a flexible tube, which tube in turn is to be attached to a cleaning port or cleaning attachment. The flexible tube allows the device to be distanced from the pillar to some extent.

In an embodiment of the present invention between the slopes a thickening or protruding section is present, wherein the thickening between the slopes comprises a plane wherein the plane runs substantially parallel to the guidance part. The plane may be substantially flat and extends between the two slopes for example. It is conceivable that the plane has a width that is equal over the length. The plane may also be slightly ribbed. This plane between the slopes provides for a good grip in a coupled position of the connector on the pillar. The ratio between smooth guidance for coupling and decoupling and a good fixation in the coupling state may be balanced by changing the angles of the slopes as well as the thickness and dimension of the thickening or protruding section. This balance is found for example in a preferred embodiment, wherein the plane of the thickening extends in the longitudinal direction over a length between 1 and 3 mm, preferably between 1.5 and 2.5 mm and even more preferably over substantially 2 mm.

In an embodiment, the thickening comprises a trapezoidal cross-section in the longitudinal direction of the pillar. The first and second slope and the plane of the thickening may form part of the trapezoid, wherein the base of the trapezium shape may be formed by the guidance part of the pillar. Such shape allows guiding over the pillar as well as resisting removal from the pillar to some extent.

In an embodiment of the present invention, the thickening extends, substantially completely, around the guidance part, thus forming a ring-shaped thickening around the pillar. The thickening is preferably uninterrupted along the circumference of the pillar. This has the advantage that it improves the sealing properties of the coupling around the complete pillar, and no channel or leak of washing or rinsing liquid occurs.

In a preferred embodiment of the present invention, the outer size of the cross-section of the thickening of the pillar is larger than the outer size of the guidance part, with the outer size of the cross-section between 1.1 and 1.5 times larger, preferably between 1.25 and 1.35 and even more preferably about 1.3 times the outer size of the guidance part. Experiments have shown that these dimensions provide good sealing properties and provide for an easy to use coupling and decoupling with the connector on the pillar. The outer size of the thickening is for instance the maximal diameter of the thickening, wherein the outer size of the guidance part is the maximal diameter of the guidance part, excluding the thickening.

To increase the ease of use even further, it is conceivable that in an embodiment of the coupling a stopping surface is located between the at least two ends of the pillar. Such stopping surface provides an indication for the connector that is coupled onto the pillar, or that the connector has progressed along a predetermined distance over the pillar. Once the connector, in particular the elbow fitting of the connector, touches the stopping surface during the coupling, this indicates that the connector is placed in the correct position for the coupled state. It also prevents that the connector is placed too far over the pillar with damage to the connector as a potential consequence. In an embodiment the stopping surface is arranged on the first slope, facing the first end, more in particular arranged on the transition of the guidance part to the first slope.

The pillar of the coupling may also be provided with a ring-shaped protrusion between the thickening and the second end, for example a ring-shaped flange, preferably with a substantially flat surface facing the first end. It is preferred that between the connector and the surface facing the first end of the pillar a small space is left open in a coupled state, to allow passage of cleansing fluid to avoid congestion of dirt between the connector and the pillar.

In a preferred embodiment of the present invention the spacing between the transition of the second slope to the plane of the thickening and the ring-shaped protrusion is substantially 6 mm in the longitudinal direction. Experiments have shown that said spacing provides good properties for the resistance caused by the second slope in the coupled state, such that the connector remains coupled while the coupling is in use for cleaning a hose by a cleaning machine.

Experiments also showed improved sealing properties for an embodiment wherein the outer size of the cross section of the thickening is substantially equal to the spacing between the transition of the second slope to the plane of the thickening and the stopping surface. For example, the diameter of the thickening, perpendicular to the longitudinal direction, is substantially equal to the spacing between the transition of the second slope to the plane of the thickening and the surface facing the first end of the pillar of the ring-shaped protrusion.

An example of an easy to use pillar with a stopping surface is a pillar wherein the first slope of the thickening serves as a stopping surface. The stopping surface preferably extends along a distance around the pillar and is uninterrupted such that is provides a stopping surface around the circumference of the pillar.

In an embodiment, the connector of the coupling comprises a tube, for example manufactured from a polymer or a plastic, in particular silicone. The use of a tube as part of the connector increases the flexibility of the material properties to use for the connector. It is conceivable that the tube is manufactured from silicone with a hardness between 65-75 Shore, preferably 69-71 Shore, even more preferably 70 Shore, these values should be read as Shore hardness on the Shore A hardness scale. This hardness is the result of experiments to determine good sealing properties but also provide for easy coupling and uncoupling. In this embodiment the silicone tube ensures a seal in cooperation with the pillar at the location of the thickening.

In a preferred embodiment, the connector comprises an elbow fitting or pipe connection and a tube. The tube and the elbow fitting cooperate and together form the connector, wherein the tube is placed around the elbow fitting before the connector is used in the coupling. The elbow fitting may be connected to a hose at one end and at the other end the elbow fitting is connected to the tube. In the coupling state the elbow fitting will touch the pillar. An indication may be present for a proper placement of the elbow fitting, for instance when the elbow fitting touches the stopping surface. The tube will touch the pillar at the location of the thickening for good sealing properties. Preferably, when the coupling is in a coupled state, a spacing is present between the head end of the tube of the connector and the pillar, preferably with the ring-shaped protrusion. The head end of the tube, the end opposite to the elbow fitting, will not touch the pillar but a small space will be present to avoid congestion of any dirt or other small particles. The small space allows cleansing fluid to pass through. It is preferred that between the connector and the surface facing the first end of the pillar a small space is left open in a coupled state, to allow passage of cleansing fluid to avoid congestion of dirt between the connector and the pillar. To allow the passage of cleansing fluid, the spacing may extend in a longitudinal direction and may have a maximum opening in the longitudinal direction of 1 mm, preferably 0.5 mm, and even more preferably maxim 0.2 mm. The side of the connector which is not to be attached to the pillar may be arranged to be coupled to a device to be cleaned, for instance to an endoscope, or to a flexible tube which is to be coupled to the device.

This type of a connector is advantageous because it allows for an easy change in orientation of two sides of the connector. One end of the connector may be aligned with the pillar, whereas another end of the connector may be arranged perpendicular to the pillar.

In an embodiment of the present invention it is conceivable that the connector is slidable over the first end of the pillar, for instance such that the connector can slide to a predetermined position in a coupled state. This predetermined position may be visible by an indicator on the connector or the pillar may be configured to indicate this predetermined position, for instance by a stopping surface or by a part of the connector touching the top of the pillar.

To increase the ease of use when coupling and decoupling it is advantageous if the connector of the coupling comprises an elbow fitting, which comprises an angle of substantially 90 degrees with the connector, for the coupling and uncoupling of a hose to a cleaning machine. This angle makes it possible to couple and decouple with one hand only, since for coupling only a movement in one direction is necessary. The pillar may for instance extend mainly vertically from the cleaning machine. The connector then also extends mainly vertically. When the connector is provided with an elbow fitting of about 90 degrees, one end of which is attached to the vertically extending connector, the other end is oriented mainly horizontally, which allows a straight tube to be connected to the horizontal end. This tube can be connected to a device to be cleaned over a horizontal distance, without risking the tube to be bent.

For proper cleaning of hoses, it is advantageous if a relatively high pressure can be used for the cleaning, while the hose remains connected to the pillar. The coupling may thus be configured to keep the connector coupled to the pillar under a working pressure of maximal substantially 1500 mbar, preferably maximally 1250 mbar, more in particular maximally 1050 mbar when a hose is coupled. On average, the working pressure will be around 1000 mbar when the device is operational, and in particular the working pressure is between 950 mbar and 1050 mbar. This is advantageously achieved by balancing the material properties of the connector as well as the angles of the surfaces of the pillar and dimension or thickness of the protruding portion of the pillar.

It is beneficial when the first end, or free end, of the guidance part is rounded. This smoothens and simplifies the set up of the connector on the pillar, in particular because it prevents the occurrence of buckling. Preferably the guidance part is rounded such that it automatically aligns the connector and the pillar, such that the connector can slide onto the pillar. The rounded portion of the guidance part may for example form part of an arc with a radius of about 0.4 mm. The rounded edge of the guidance part also facilitates correct alignment onto the guidance part.

For a user of the coupling according to the present invention, it is possible to couple a hose with one hand only, as the coupling may be configured for the decoupling of the connector with a maximum force of 30N, preferably maximum force of substantially 15N in a wet condition and a maximum force of 25N when in dry condition. These relative low forces allow repetitive use of the coupling and complies with most working conditions.

The invention also relates to a cleaning machine for the cleaning of one or more hoses provided with a coupling according to the present invention. In an embodiment of the cleaning machine it is possible that multiple pillars are positioned next to each other, preferably wherein each pillar is provided with a corresponding connector. This way, multiple hoses may be cleaned simultaneously which increases the productivity of the cleaning machine The invention also relates to a pillar for a coupling for the coupling of one or more hoses to a cleaning machine.

BRIEF DESCRIPTION OF THE DRAWINGS

The invention will be further elucidated by several examples and with reference to the appended figures, wherein FIG. 1 schematically shows an embodiment of part of a coupling according to the present invention.

DETAILED DESCRIPTION

In above mentioned figures the same reference numbers are used for equivalent features.

Figure 1:
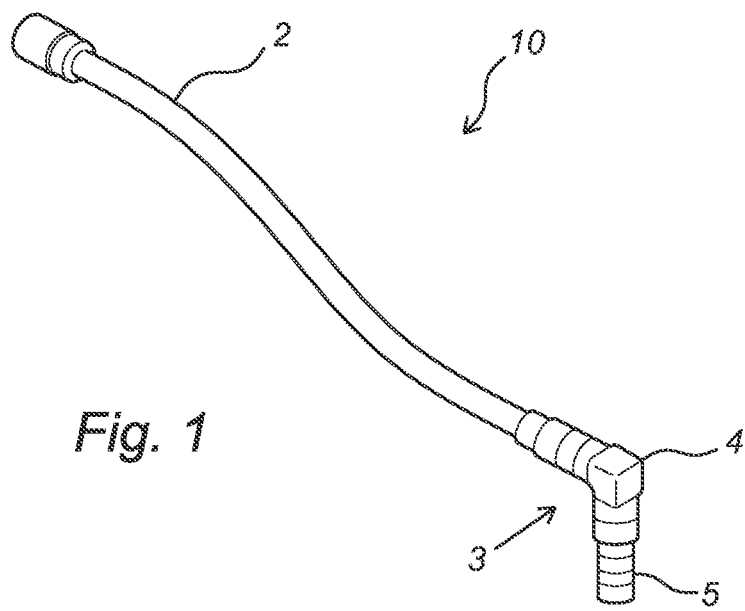
Figure 2:
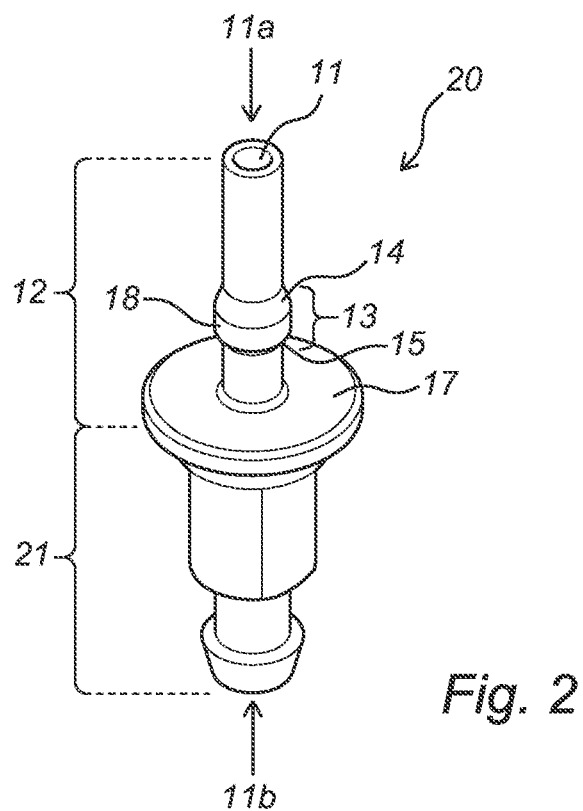
FIG. 2 shows an embodiment of a pillar according to the present invention.

FIG. 1 schematically shows an embodiment of part of a coupling 10 of a hose 2 for use in an endoscope to a connector 3 for connecting the hose to be cleaned with a pillar (shown in FIG. 2). In this embodiment the connector 3 comprises two elements, an elbow fitting 4 making an angle of substantially 90 degrees and a silicone tube 5. The hose 2 plus connector 3 may be connected to a pillar as shown in FIG. 2. A cross-section of the total coupling using this part of an embodiment according to the present invention is shown in FIG. 3.

FIG. 2 shows an embodiment of a pillar 20 for a coupling according to the present invention. The pillar 20 comprises a longitudinal hollow body 11 with at least two open ends 11a and 11b for guiding a cleaning liquid from a cleaning machine through the pillar towards a hose to be cleaned, wherein the open end 11b is coupled to the cleaning machine and the opposite end 11a to the connector 3 (as shown in FIG. 3). The longitudinal hollow body 11 comprises a substantially longitudinal guidance part 12, located towards the first end 11a, for the guidance of the connector 3 onto the pillar 20. The guidance part 12 is provided with a thickening 13 for fixing the connector to the guidance part 12. The connection of the connector 3 onto the pillar 20 may be done by sliding the connector 3 over the guidance part 12 onto the pillar 20. The thickening 13 in this embodiment is provided with a first slope 14 facing the first end 11a with an angle of substantially 20 degrees for guiding the connector over the thickening 13 during coupling. The thickening 13 also comprises a second slope 15 of substantially 45 degrees, which slope 15 creates a predetermined resistance to prevent undesired shifting of the connector with the pillar 20, or worst case from the pillar 20 while cleaning. The resistance of the second slope 15 is chosen such that the resistance can be overcome by one hand during decoupling. The thickening 13 extends around the guidance part 12 of the pillar 20 in a ring-shaped form for improved sealing properties. In this embodiment the end of the guidance part 12 is defined by a ring-shaped protrusion 17 located between the two ends 11a, 11b, for indicating that the connector 3 is at its position for a correct coupling. The part 21 of the pillar on the side of the ring-shaped protrusion 17 opposite to the guidance part 12 is used for a connection with a cleaning machine. This part 21 of the pillar 20 may have various shapes that are corresponding with the connection to the cleaning machine.

Figure 3:
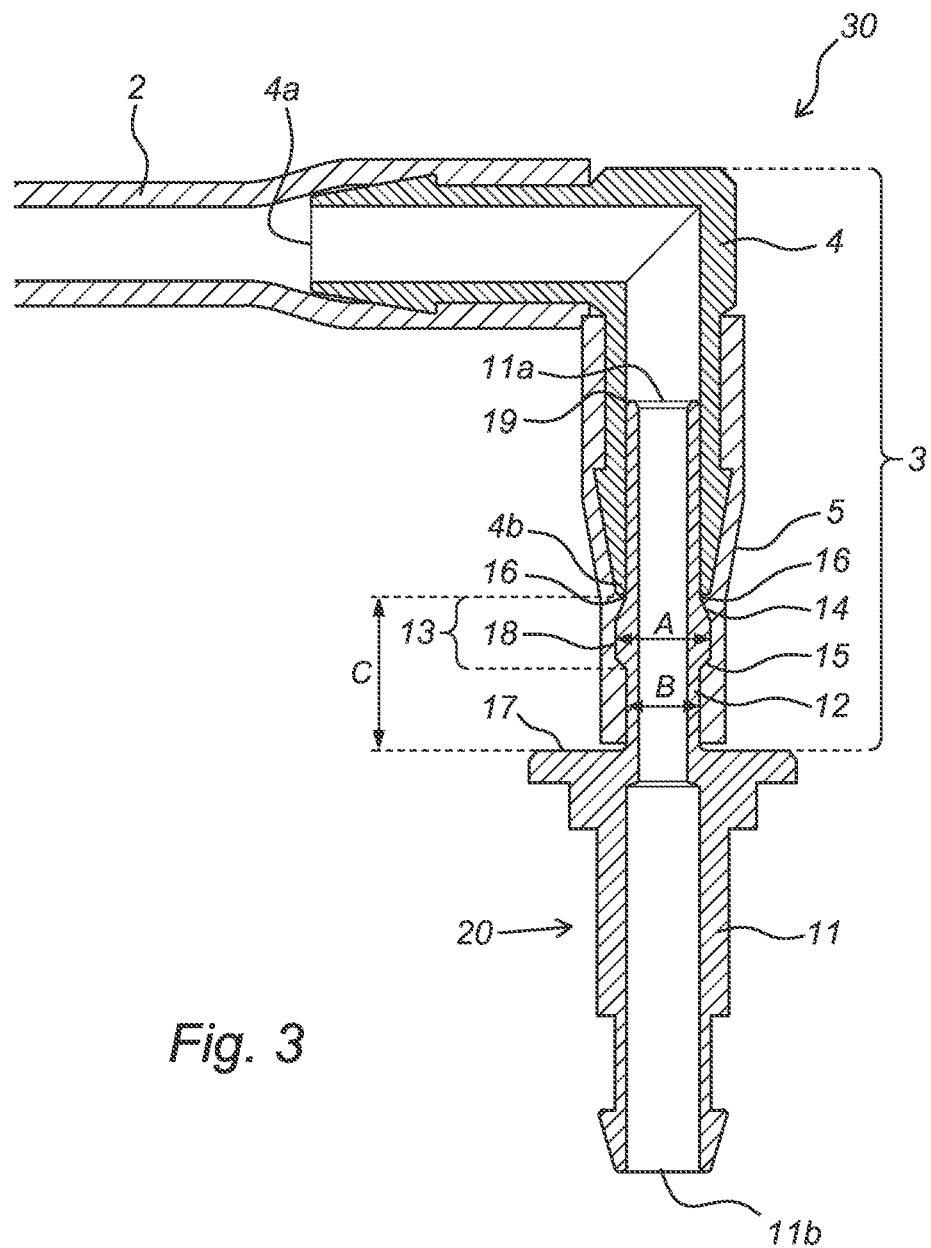
FIG. 3 schematically shows a cross-section of an embodiment of a coupling according to the present invention.

FIG. 3 shows a cross-sectional view of an embodiment of a coupling 30 according to the present invention, using the embodiment of the pillar 20 from FIG. 2 and the connector 3 and hose 2 as shown in FIG. 1. In this figure it is clearly shown that the connector 3 comprises two elements, an elbow fitting 4 with an angle of approximately 90 degrees and a silicone tube 5. The material properties of the tube 5 and the angles of the slopes 14, 15 are selected based on the desired resistance during coupling, uncoupling and operation. The elbow fitting 4 comprises a hollow body for guidance of the cleaning liquid. The hollow body has two ends 4a and 4b and is provided with slopes on the outside of both ends for a proper connection with the hose 2 on one end 4a and the silicone tube 5 at the other end 4b. The connector 3 connects the hose 2 to the pillar 20, which pillar can be connected to a cleaning machine. To make the connection of the connector 3 with the pillar 20, the connector 3 is slid onto the guidance part 12 over the thickening 13 for fixing of the connector 3 onto the pillar 20. In this embodiment the thickening 13 also provides a sealing location to prevent leakage of cleaning liquid during operation. The thickening 13 comprises a plane 18 between the slopes 14, 15 wherein the plane 18 runs substantially parallel to the tangential line of the guidance part 12. The cross-section shows that the thickening 13 also has a trapezoidal cross-section with its base aligned with the guidance part 12 and wherein the plane 18 forms the top of the trapezium shape. The slopes 14, 15 form part of the trapezium shape as well, with the slope 14 having an angle of 20 degrees between the tangential line of the slope 14 and the tangential line of the guidance part 12 and the slope 15 with an angle of 45 degrees between the tangential line of the slope 15 and the tangential line of the guidance part 12. The end 11a of the pillar 20 is rounded for improved alignment of the connector 3 with the pillar 20 for coupling. The rounded portion 19 of the guidance part 12 forms part of an arc with a radius of about 0.4 mm. The connector is positioned properly when the elbow fitting 4 is stopped by the stopping surface 16. Between the silicone tube 5 of the connector 3 and the ring-shaped surface facing the first end of the ring-shaped protrusion 17 a small space is visible. This small space is used for cleansing fluid to avoid accumulation of dirt on the pillar. In this embodiment the outer size A of the cross-section of the thickening 13 of the pillar is larger than the outer size B of the guidance part 12, with the outer size A approximately 1.3 times the outer size B of the guidance part 12. In this embodiment the outer size A is 6 mm, the outer size B is 4.6 mm and the spacing between the stopping surface 16 and the surface of the ring-shaped protrusion 17 facing the first end 11a is around 10 mm. In this shown embodiment the distance C between the stopping surface 16 and the surface of the ring-shaped protrusion 17 facing the first end, is substantially 10 mm.

Figure 4:
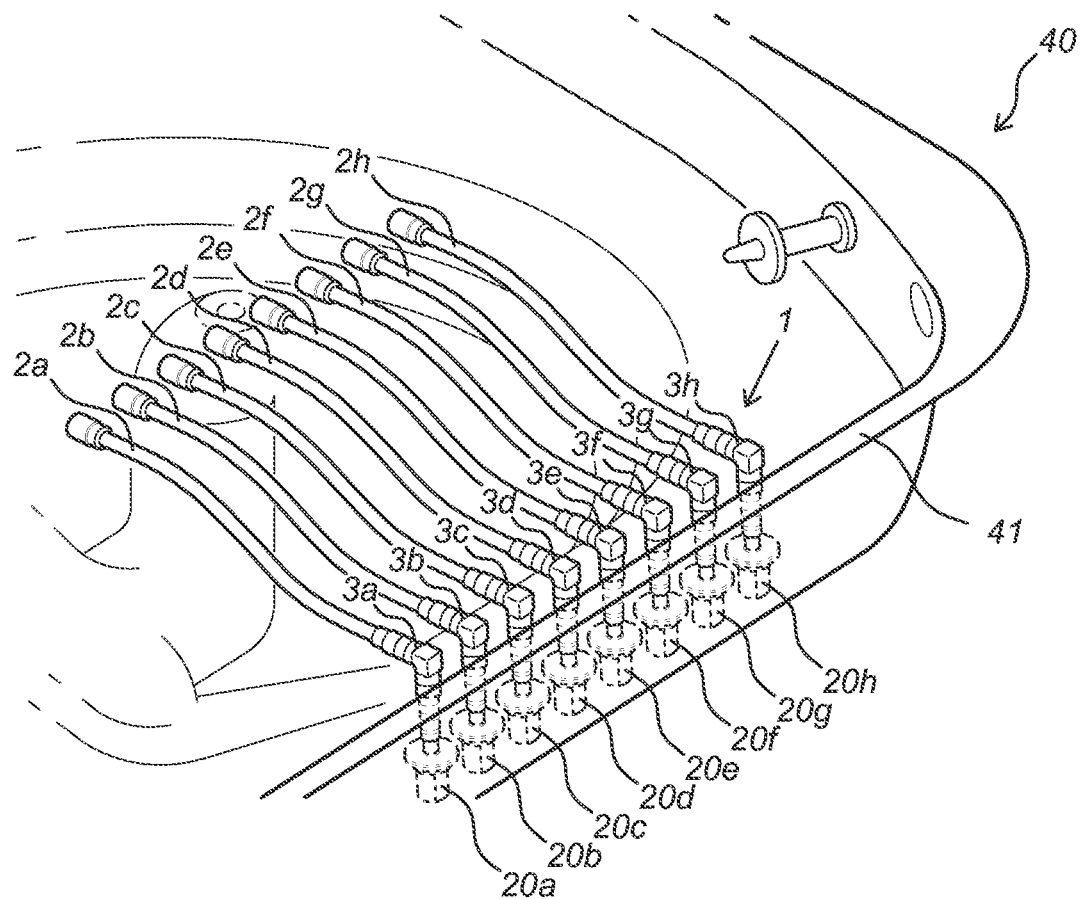
FIG. 4 shows a part of a cleaning machine according to the present invention comprising multiple pillars, each connected to a hose.

FIG. 4 shows an embodiment of a cleaning machine 40 according to the present invention. In the housing 41 of the machine 40 multiple pillars 20a, 20b, 20c, 20d, 20e, 20f, 20g, 20h are connected to the cleaning machine 40, wherein each pillar 20a, 20b, 20c, 20d, 20e, 20f, 20g, 20h extends vertically from the housing 41 of the cleaning machine 40. Each pillar 20a, 20b, 20c, 20d, 20e, 20f, 20g, 20h is connected to a hose 2a, 2b, 2c, 2d, 2e, 2f, 2g, 2h via a connector 3a, 3b, 3c, 3d, 3e, 3f, 3g, 3h, wherein each connector has an angle of approximately 90 degrees. In this figure it is shown that due to the 90 degrees angle of the connector 3a, 3b, 3c, 3d, 3e, 3f, 3g, 3h, each hose 2a, 2b, 2c, 2d, 2e, 2f, 2g, 2h may be cleaned in a horizontal way without bending of the hose 2a, 2b, 2c, 2d, 2e, 2f, 2g, 2h. Due to this configuration multiple hoses 2 may be connected in an efficient way to a cleaning machine.

The above described figures are meant for illustrative purposes and are not limitative to the invention as claimed in the following claims.

The invention claimed is:
1. A coupling for coupling of one or more hoses to a cleaning machine, comprising:
   at least one connector for connecting a hose to be cleaned with a pillar; and
   at least one pillar for connection of the at least one connector with the cleaning machine, wherein the pillar comprises a longitudinal hollow body with at least two open ends comprising:
      a substantially longitudinal guidance part, situated towards a first end, for the guidance of the connector over the pillar; and
      a second end opposite to the first end in a longitudinal direction, for connecting the pillar to the cleaning machine, and
   wherein the guidance part is provided with a thickening for the fixing of the connector to the guidance part, wherein the thickening comprises:
      a first slope facing the first end, which slope has an angle with the guidance part between 5 and 45 degrees for guiding the connector over the thickening from the first end of the guidance part;
      a second slope facing the second end, which slope has an angle with the guidance part between 30 and 60 degrees for creating a predetermined resistance to prevent undesired shifting of the connector over the pillar; and
      a plane located between the first and second slopes, wherein the plane runs substantially parallel to the guidance part, wherein the plane and the first and second slopes form a continuously raised platform immediately bounded on either side by the first and second slopes, and
   wherein the pillar is provided with a ring-shaped protrusion between the thickening and the second end, the ring-shaped protrusion having a first side and a second side opposite the first side, where the first side is located proximate to the thickening and is formed from a substantially vertical face.

2. The coupling according to claim 1, wherein the plane extends in the longitudinal direction over a length between 1 and 3 mm.

3. The coupling according to claim 1, wherein the thickening comprises a trapezoidal cross-section in the longitudinal direction of the pillar and/or wherein the thickening extends around the guidance part.

4. The coupling according to claim 1, wherein an outer size of the cross-section of the thickening of the pillar is larger than an outer size of the guidance part, with the outer size of the cross-section between 1.1 and 1.5 times larger than the outer size of the guidance part.

5. The coupling according to claim 1, wherein a stopping surface is located between the at least two ends.

6. The coupling according to claim 1, wherein the ring-shaped protrusion is a ring-shaped flange.

7. The coupling according to claim 1, wherein the ring-shaped protrusion comprises a substantially flat surface facing the first end.

8. The coupling according to claim 1, wherein the connector comprises an elbow fitting and/or a tube.

9. The coupling according to claim 8, wherein the connector comprises a tube, wherein the tube is manufactured from a polymer or a plastic.

10. The coupling according to claim 8, wherein the connector comprises a tube, wherein the tube is manufactured from silicone with a hardness between 65-75 Shore on a Shore A hardness scale.

11. The coupling according to claim 1, wherein the connector comprises a tube, wherein in a coupled state a spacing is present between the head end of the tube of the connector and the pillar.

12. The coupling according to claim 11, wherein the spacing extends in the longitudinal direction and has a maximum opening in the longitudinal direction of 1 mm.

13. The coupling according to claim 1, wherein the connector is slidable over the first end of the pillar, such that the connector can be slid to a predetermined position in a coupled state.

14. A cleaning machine for the cleaning of one or more hoses provided with a coupling according to claim 1, wherein multiple pillars are positioned next to each other.

* * * * *